(12) United States Patent
Fraga et al.

(10) Patent No.: US 11,260,367 B2
(45) Date of Patent: Mar. 1, 2022

(54) CATALYTIC SYSTEM AND PROCESS FOR THE PRODUCTION OF LIGHT OLEFINS FROM ETHANOL

(71) Applicants: Instituto Nacional de Tecnologia, Rio de Janeiro (BR); Braskem S.A., Camacari (BR)

(72) Inventors: Marco Andre Fraga, Rio de Janeiro (BR); Lucia Gorenstin Appel, Rio de Janeiro (BR); Alexandre Barros Gaspar, Rio de Janeiro (BR); Felipe Jorge Lima da Silveira, Rio de Janeiro (BR); Andrea Maria Duarte de Farias, Rio de Janeiro (BR); Clarissa Perdomo Rodrigues, Rio de Janeiro (BR); Fabio Bellot Noronha, Niteroi (BR); Roberto Werneck do Carmo, Campinas (BR); Andrea Marins de Oliveira, Porto Alegre (BR); Luiza Roza, Porto Alegre (BR)

(73) Assignees: Instituto Nacional de Tecnologia, Rio de Janeiro (BR); Braskem S.A., Camaçari (BR)

( * ) Notice: Subject to any disclaimer, the term of this patent is extended or adjusted under 35 U.S.C. 154(b) by 84 days.

(21) Appl. No.: 16/217,385

(22) Filed: Dec. 12, 2018

(65) Prior Publication Data

US 2020/0188882 A1 Jun. 18, 2020

(51) Int. Cl.
*B01J 21/04* (2006.01)
*B01J 21/06* (2006.01)
(Continued)

(52) U.S. Cl.
CPC .............. *B01J 21/04* (2013.01); *B01J 8/001* (2013.01); *B01J 21/066* (2013.01); *B01J 23/10* (2013.01);
(Continued)

(58) Field of Classification Search
CPC . B01J 21/04; B01J 21/066; B01J 23/10; B01J 35/02; C07C 1/24
See application file for complete search history.

(56) References Cited

U.S. PATENT DOCUMENTS 4,120,909 A * 10/1978 Amirnazmi ............... C07C 1/24
585/437
4,232,179 A 11/1980 Valladares Barrocas et al.
(Continued)

FOREIGN PATENT DOCUMENTS

CN 101121625 A 2/2008
CN 101244971 A 8/2008
(Continued)

OTHER PUBLICATIONS

Rodrigues et al., Chemicals from ethanol—The acetone one-pot synthesis, Applied Catalysis A: General 458 (2013), p. 111-118.
(Continued)

*Primary Examiner* — Cam N. Nguyen
(74) *Attorney, Agent, or Firm* — Duane Morris LLP

(57) ABSTRACT

The present invention relates to a catalytic system for the preparation of light olefins through the dehydration of alcohols, including at least one catalyst and at least one co-catalyst, wherein the catalyst is selected from among catalysts for the catalytic dehydration of ethanol and with the co-catalyst selected from among oxy-ketonization reaction catalysts, wherein the catalyst:co-catalyst mass ratio is within a range of 0.5:0.125 to 2:10, and preferably within a range of 1:0.25 to 1:5.

11 Claims, 1 Drawing Sheet

(51) Int. Cl.
  *B01J 23/10* (2006.01)
  *B01J 35/02* (2006.01)
  *C07C 1/24* (2006.01)
  *B01J 37/00* (2006.01)
  *B01J 8/00* (2006.01)
  *C07C 11/04* (2006.01)

(52) U.S. Cl.
  CPC ............ *B01J 35/02* (2013.01); *B01J 37/0063* (2013.01); *C07C 1/24* (2013.01); *B01J 2208/00017* (2013.01); *B01J 2208/00539* (2013.01); *B01J 2208/025* (2013.01); *C07C 11/04* (2013.01); *C07C 2521/04* (2013.01); *C07C 2521/06* (2013.01)

(56) References Cited

U.S. PATENT DOCUMENTS

| | | | | |
|---|---|---|---|---|
| 4,301,319 | A * | 11/1981 | Greene | C07C 1/24 585/638 |
| 4,302,357 | A | 11/1981 | Kojima et al. | |
| 6,818,589 | B1 * | 11/2004 | Gillespie | B01J 21/066 502/302 |
| 7,700,816 | B2 * | 4/2010 | Xu | B01J 21/063 502/214 |
| 9,180,430 | B2 * | 11/2015 | Liu | B01J 37/04 |
| 10,005,702 | B2 * | 6/2018 | Spannhoff | C07C 1/22 |
| 10,407,356 | B2 * | 9/2019 | Partington | C07C 1/24 |
| 10,815,167 | B2 * | 10/2020 | Ramachandran | B01J 21/063 |
| 2003/0065233 | A1 * | 4/2003 | Fuji | C07C 1/20 585/639 |
| 2012/0238792 | A1 * | 9/2012 | Watson | C07C 5/05 585/277 |
| 2018/0002249 | A1 * | 1/2018 | Vecchini | B01J 37/031 |
| 2019/0046967 | A1 * | 2/2019 | Li | C07C 31/10 |
| 2020/0048170 | A1 * | 2/2020 | Li | C07C 1/20 |

FOREIGN PATENT DOCUMENTS

| | | |
|---|---|---|
| CN | 101439294 A | 5/2009 |
| CN | 102190543 A | 9/2011 |
| CN | 102372558 A | 3/2012 |
| CN | 102671689 A | 9/2012 |
| CN | 103121900 A | 5/2013 |
| CN | 104084182 A | 10/2014 |
| CN | 104557394 A | 4/2015 |
| WO | 2011002699 A2 | 1/2011 |
| WO | 2014171688 A1 | 10/2014 |

OTHER PUBLICATIONS

De Lima et al., The first step of the propylene generation from renewable raw material: Acetone from ethanol employing CeO2 doped Ag, Catalysis Today 279 (2017), p. 252-259.

* cited by examiner

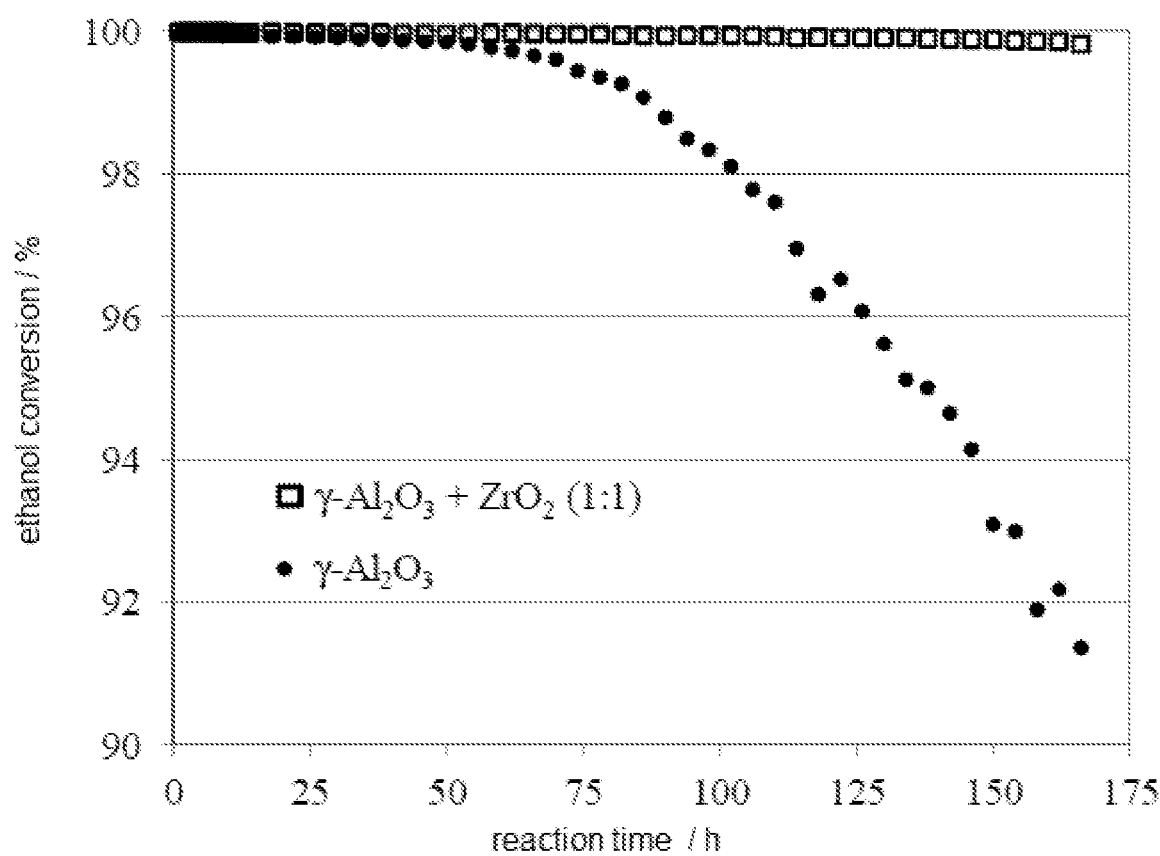

CATALYTIC SYSTEM AND PROCESS FOR THE PRODUCTION OF LIGHT OLEFINS FROM ETHANOL

FIELD OF THE INVENTION

The present invention relates to the field of catalysts for the production of light olefins, and in particular to an ethanol dehydration system and process using co-catalysts in a catalytic reaction.

BACKGROUND OF THE INVENTION

Ethene is the most important platform molecule for the petrochemical industry. Its main application consists of the fabrication of polyethylene, which is widely used in packaging by the food industry. This polymer is also used to make storage drums, household goods, water, gas and irrigation pipes, garbage bags, industrial coatings and many other applications. It is also worth mentioning its application for generating a wide variety of important petrochemical products and/or intermediate goods such as ethylene oxide, ethylene glycol, styrene vinyl chloride, acrylate and others.

The production of this olefin is handled through routes that are widely known and used at the industrial level. Noteworthy among them is steam cracking, which may use a vast range of raw materials such as petrochemical naphtha, light refinery gases and shale gas.

Rising concerns over sustainability and particularly the reduction of greenhouse gases have prompted the chemical industry to seek out renewable raw materials. In this context, the use of ethanol made from biomass became a particularly interesting option, due to the widespread production of this alcohol in Brazil and its growth potential through second-generation ethanol made from lignocellulosic wastes.

Ethene production is handled through the ethanol dehydration reaction in the presence of a heterogeneous acid catalyst. One of the main technical problems in this process is the generation of some by-products, whose presence in the system affects olefin production costs. Acetaldehyde is rated as an unfavorable contaminant, as it decomposes under reaction conditions, generating residues on the catalyst surface, which leads to its deactivation, thus shortening its useful lifespan. As a result, catalyst regeneration is regularly required, causing halts in the process and additional costs. The formation of ethane as a by-product is also unwanted as, although inert, its presence increases separation costs. There is no doubt that lessening acetaldehyde and ethane concentrations in the reaction system will result in lower operating costs.

The present invention is focused on the removal of unwanted by-products. Specifically, the invention allows avoidance or reduction of the secondary formation of acetaldehyde and ethane.

U.S. Pat. No. 4,232,179 was the first to describe an adiabatic process for converting ethanol to ethene using silica-alumina and alumina catalysts. In the examples given in this patent, the reaction was initiated at temperatures between 390° C. and 470° C. and an inert/ethanol ratio between 2.85 and 7.15 by mass. Example 13 in this patent shows a higher conversion using alumina, fed with a mixture of water and ethanol with a mass ratio of 3:1, inflow temperature of 470° C. and a final temperature of 360° C. when leaving the reactor.

Some references—such as CN 104557394 and CN 102372558 for example—describe methods that optimize the mode of operation and the configuration of industrial plants, using power co-generation to lower energy costs. These references describe the steps in the ethene production route without modifying the catalyst.

U.S. Pat. No. 4,302,357 mentions the operating conditions and the short useful life of the catalyst resulting from carbon deposits on its surface, as disadvantages of the ethanol dehydration process. In order to prevent this deactivation that would result from the presence of olefins formed in parallel reactions, according to the authors, the invention suggests the use of alumina catalysts containing some specific oxides. Similarly, the most recent document—CN 102190543—also reports deactivation problems, although caused by $CO_2$ and $H_2$ as by-products CO, upgrading the reaction through the preparation of a new catalyst containing a metal oxide selected from Groups IA or IIA and alumina. Those proposals suggest new catalysts for ethanol dehydration and indicate different by-products as agents causing catalyst deactivation, making no reference to acetaldehyde.

Following this same direction, document CN 101121625 refers to an ethene preparation method through ethanol dehydration, proposing a reduction in the energy consumption of the reaction through using $SiO_2/Al_2O_3$. Document CN 102671689 describes an ethene dehydration method for different ethanol concentrations and a catalyst preparation model using a catalyst with a USY base enriched with a transition metal. Document CN 101244971 describes a method synthesizing bioethanol dehydration in ethene, in order to make the process cheaper and more efficient through a catalyst with a modified zeolite base.

Still regarding the use of a single catalysis system, CN 101439294 and WO 2014171688 were retrieved. The invention described in document CN 101439294 refers to an ethylene preparation technology through ethanol dehydration. The main component of the catalyst is ZSM-5 with the addition of one or two elements selected from among aluminium, magnesium, phosphorus and lanthanum, in order to promote catalytic activity. Document WO 2014171688 describes an ethanol dehydration catalyst for converting a raw material that comprises anhydrous or hydrated ethanol in ethylene, wherein the ZSM-5 contains 0.1-0.5% by weight of lanthanum (La) or 0.05 to 1% by weight of gallium (Ga). It is apparent from the state of the art that these alterations (in both documents) are intended to control the acidity of zeolite, as they are generally very acidic. This characteristic triggers reactions leading to heavy compounds that deactivate the catalyst, not fostering the formation of ethene and leading to a dehydration reaction that extends well beyond the output of the desired product.

Documents CN 101121625, CN 102671689, CN 101244971, CN 101439294 and WO 2014171688 present catalysts or catalytic systems that may be used in the system proposed in this invention; however, they would not prevent the formation of acetaldehyde, which is an unwanted by-product of the ethanol dehydration reaction.

Document WO 2011002699 describes a process for preparing olefins from aliphatic alcohols, using catalysts that may contain alumina, silica-alumina and zirconia, among others. Nevertheless, although mentioning the use of oxides, this reference addresses the ethanol dehydration reaction in two steps, using separate reactors forming ethyl ether in the presence of a dehydration catalyst in the first reactor at a temperature of 200° C. to 450° C., and placing it to react in a second reactor operating at a higher temperature level than the first reactor, in the presence of a second dehydration catalyst. The document also reports that this temperature system helps reduce the formation of by-products, which in turn lessens the formation of coke, encrustations, and the need to use large amounts of water, thus lowering energy and capital costs. However, it may be noted from the state of the art that using two reactors requires heavier investments and higher production costs than using just one reactor, which might in turn not be offset through reduced water use.

Current research in this field describes new catalysts that require meticulous preparation. Already costly, the process requires commercial catalysts such as alumina and silica-alumina that are already efficient, although subject to deactivation through the formation of by-products. From this standpoint, documents CN 104084182 and CN 103121900 describe the development of catalysts with larger pore volumes, greater surface areas and enhanced hardness than the usual alumina catalyst used for ethanol dehydration, through modifications to the preparation process. These catalysts present greater activity under certain conditions, with better ethene selectivity and longer useful lifespans, in other words, they are more stable than conventional alumina. Furthermore, enhanced hardness is very convenient for use in a fluid bed reactor. However, these documents do not provide clear data on the extension of the useful lives of the catalysts.

The use of zeolites for ethanol transformation is widely described in the scientific literature. In general, the formation of ethene, propene and heavy compounds is observed. The latter are precursors of coke, which causes the deactivation process, greatly shortening the useful lives of these zeolite-based catalysts. By adjusting the operating conditions and acid strength of these materials, it is possible to reduce this effect. However, due to the nature of these catalysts, this issue must always be present.

From a technological standpoint, current industrial dehydration processes for short-chain alcohols operate reliably and with good results. Ethene production processes using fossil-based raw materials are generally fine-tuned, leading to lower production costs. Without doubt, they establish a production costs threshold that drives improvements in processes for obtaining ethene through ethanol.

Although current catalysts are efficient, they are subject to limitations, due to the inevitable formation of by-products to even in small quantities. In addition to representing a loss of part of the green carbon supplied by the alcohol, these by-products affect catalyst performance, leading to higher operating costs.

Formed as a by-product during ethanol dehydration using ethene, acetaldehyde is an important dehydration catalyst deactivation agent. Hydrogen, ethane and other by-products may also be formed, usually generated from degraded acetaldehyde.

C. P. Rodrigues, P. C. Zonetti, C. G. Silva, A. B. Gaspar, L. G. Appel, *Applied Catalysis A: General*, Vol. 458, 2013, 111 to 118 doi:10.1016/j.apcata.2013.03.028) and A. F. F. de Lima, P. C. Zonetti, C. P. Rodrigues, L. G. Appel, available online on May 26, 2016, *Catalysis Today*, doi:10.1016/j.cattod.2016.04.038, recently showed that certain catalysts can transform ethanol into acetone in the presence of water. These authors also ascertained that acetaldehyde is one of the intermediate products in this reaction.

The purpose of the present invention is to thus provide a new catalytic process and systems for the production of olefins through dehydrating alcohols with higher performance, avoiding and/or reducing the formation of by-products during the reaction, with a high conversion rate and high selectivity for olefins.

This purpose is achieved through this invention by means of a catalytic system comprising at least one catalyst and at least one co-catalyst, wherein the catalyst causes the dehydration of the alcohol into olefin and the co-catalyst prompts the oxy-ketonization reaction, in other words, through adsorption and transformation of generated by-products into substances that are less harmful, particularly the uptake and transformation of acetaldehyde into acetone.

Surprisingly, the addition of a new component (the co-catalyst) to the catalytic system resulted in longer usage time for the catalyst and an increase in its deactivation resistance, although without lowering the ethene selectivity and ethanol conversion values; in other words, the addition of a co-catalyst enhancing the efficiency of the ethanol dehydration reaction. Moreover, an improvement is noted in the dehydration reaction selectivity through the partial removal of an unwanted by-product that causes undesired reactions when present in the reaction environment; its removal thus leads to more favorable operating costs.

As there is no need for modification to the composition of the commercial catalysts nor any rearrangement of the plant operating mode configuration, the process of the present invention also differs from the documents constituting the state of the art.

SUMMARY OF THE INVENTION

The present invention relates to a catalytic system for the preparation of light olefins through the dehydration of alcohols, comprising at least one catalyst and at least one co-catalyst, wherein the catalyst is selected from among catalysts for the catalytic dehydration of ethanol and with the co-catalyst selected from among oxy-ketonization reaction catalysts, wherein the catalyst:co-catalyst mass ratio is within a range of 0.5:0.125 to 2:10, and preferably within a range of 1:0.25 to 1:5.

With the catalyst selected from the catalysts for the catalytic ethanol dehydration, namely, oxides, molecular sieves, zeolites, metal salts, ion-exchange resins, activated carbon, α-boron and $WS_2$, and the selected co-catalyst being an oxy-ketonization reaction catalyst selected from among simple or mixed oxides, including the different polymorphic structures of a simple oxide, comprising at least one metal selected from among transition metals in Groups 1B, 2B, 3B, 4B, 5B, 6B and 7B of the Periodic Table, lanthanides and metals in Groups 3A and 4A, it may be selected from the group that comprises zirconium oxide, yttrium oxide, mixed lanthanum and zirconium oxide and mixtures thereof.

Another purpose of this invention is the catalytic system, characterized in that it is a physical mixture of the catalyst and the co-catalyst consisting of pellets of each one of the components in isolation, or a pellet made from a mixture of the two components in the form of sequential layers or beds, mixed or not, or in the form of powder, wherein the particles may contain both the catalysts or individual particles of each one of the components.

Another purpose of this invention is the process for the production of light olefins from ethanol, using an alcohol flow, hydrated or not, in the presence of the catalytic system, at a temperature varying between 200° C. and 800° C., preferably between 360° C. and 470° C., and at a pressure varying between 1 bar and 60 bar, preferably 1 bar and 20 bar, wherein the hydrated alcohol presents a water:alcohol mass ratio of between 0.25:1 and up to 5:1, preferably between 1:1 and 3:1, occurring in a Plug Flow Reactor (PFR), fixed or fluid bed, batch or Continuous-Stirred Tank Reactor (CSTR), being adiabatic or not, wherein use of the catalytic system presents alcohol conversions of at least 97%, preferably 99%, and olefins selectivity of at least 97%, preferably 99%, and the catalytic system operates continuously without deactivation for a period more than five times longer than the useful life of the dehydration catalyst when used alone, in other words, without the co-catalyst.

BRIEF DESCRIPTION OF THE DRAWINGS

In order to illustrate more clearly and objectively the technical solutions shown in the examples of the invention, a brief presentation of the appended drawing is given, for one embodiment of the invention.

FIG. 1 shows an ethanol conversion progress over time for a conventional ethanol dehydration catalyst (y-alumina) and a catalyst:co-catalyst mixture with $ZrO_2$ in a proportion of 1:1, as an example.

DETAILED DESCRIPTION OF THE INVENTION

The present invention is based on the use of a mixture of a catalyst dehydrating ethanol into ethene and one co-catalyst causing oxy-ketonization, in other words, transforming the acetaldehyde formed during the process into acetone, thus giving rise to a catalytic system and process for the production of light olefins from ethanol.

The present invention relates to a catalytic system for the preparation of light olefins from the dehydration of alcohols comprising at least one catalyst and at least one co-catalyst. Light olefins are taken to mean olefins containing 2 to 6 carbon atoms, preferably ethene. The catalyst:co-catalyst mass ratio is between 0.5:0.125 to 2:10, preferably within a range of 1:0.25 to 1:5.

For the dehydration catalyst addressed by this invention, a catalyst is used for the catalytic dehydration of ethanol, namely, oxides, molecular sieves, zeolites, metal salts, ion-exchange resins, activated carbon, α-boron, $WS_2$, alumina modified by different chemical elements or aluminosilicates.

As a co-catalyst, the use of an oxy-ketonization reaction catalyst is proposed, which may be simple oxides or mixed oxides, in addition to also considering the different polymorphic ruptures of a single oxide. For the co-catalyst, it is important that it has a high specific area and is heat-stable up to at least 500° C., with basic surface sites.

In a preferred embodiment, the co-catalyst comprises at least one oxide of a metal selected from among the transition metals in Groups 1B, 2B, 3B, 4B, 5B, 6B and 7B of the Periodic Table, lanthanides and metals in Groups 3A and 4A. In a second preferred embodiment of the invention, the co-catalyst is selected from the group that comprises zirconium oxide, yttrium oxide, mixed lanthanum and zirconium oxide and mixtures thereof. The co-catalyst used in this invention causes the oxy-ketonization reaction, which refers to the acetaldehyde transformation forming acetone, $CO_2$ and $H_2$.

The catalytic system addressed by this invention may be prepared through a physical mixture of at least one catalyst and at least one co-catalyst, which may be in the form of pellets, either as pellets with each one of the components in isolation, meaning catalyst pellet+co-catalyst pellet, or a single pellet blending both of them. It may also be in the form of sequential layers or beds, not necessarily mixed. They may also be used in the form of powder, wherein the particles may contain both the catalysts or individual particles of each one of the components.

Furthermore, this invention refers to a process for the production of light olefins through dehydrating alcohols using an alcohol flow in contact with the catalytic system.

The dehydration reaction may occur in a reactor at a temperature varying between 200° C. and 800° C., preferably between 360° C. and 470° C., and at a pressure varying between 1 bar and 60 bar, preferably 1 bar and 20 bar.

The alcohol used in the process addressed by this invention may be comprised of 2 to 6 carbon atoms, and may be hydrated or not. When hydrated alcohol is used, the water:alcohol mass ratio is between 0.25:1 and up to 5:1, preferably between 1:1 and 4:1. The reaction occurs in a reactor as described above, which may be a Plug Flow Reactor (PFR), fixed or fluid bed, batch or Continuous-Stirred Tank Reactor (CSTR), being adiabatic or not.

Through using the catalytic system addressed by this invention, it is possible to convert alcohols to olefins at 97% at least and preferably 99%, and with olefin selectivity of at least 97%, preferably 99%.

EXAMPLES

The following examples are merely illustrative and are not intended to curtail the scope of the protection sought for this invention.

Performance tests of the catalytic system (catalyst+co-catalyst) were run under conditions representing the industrial process as set forth in U.S. Pat. No. 4,232,179 (example 13). An inflow was used containing a water/ethanol mass ratio of 3 and a reaction temperature of 470° C. The laboratory tests were conducted under isothermal conditions, thus keeping the reactor at 470° C. for the entire duration of the experiment. It is appropriate to mention that there is a temperature variation along the reactor for the adiabatic process, due to the endothermal reaction. In order to evaluate the performance of the catalytic systems proposed in the invention, tests were also conducted under isothermal conditions at a lower temperature (360° C.). Finally, it is noted that the performance of the catalytic systems proposed in the invention was compared on the same laboratory scale with a typical catalyst used for producing ethene from ethanol, namely alumina.

The performance of ten different co-catalysts were evaluated, and may be organized into three groups: simple oxides ($ZrO_2$, $TiO_2$, $Y_2O_3$ and $CeO_2$), simple oxide polymorphs ($ZrO_2$ with a monocline crystal structure, m-$ZrO_2$, and with a tetragonal crystal structure, t-$ZrO_2$) and mixed/doped oxides ($Y_2O_3$—$ZrO_2$, $La_2O_3$—$ZrO_2$, $TiO_2$—$ZrO_2$, $SiO_2$—$ZrO_2$ and Ag—$CeO_2$). Many of these materials are available commercially, with only $Y_2O_3$, $CeO_2$ and Ag—$CeO_2$ synthesized in the laboratory.

In all tests conducted at the higher temperature (470° C.), ethanol conversion exceeded 97%, with ethene selectivity between 97% and 99%. When using only the dehydration catalyst (alumina), the formation of acetaldehyde and ethane occurred, with selectivities between 1% and 2% and 0.1% to 0.2%, respectively. In contrast, when using the catalyst and co-catalyst system, acetaldehyde selectivity fell below 0.3%, with the formation of this aldehyde not even detected in some examples. Ethane production also dropped, with selectivities between 0.05% and 0.2%.

With the alumina and m-$ZrO_2$ system, tests were conducted with different catalyst:co-catalyst proportions, namely: 1:0.5, 1:1, 1:2, 1:3 and 1:5. No modifications in ethanol conversion into ethene were observed for any of these proportions, with olefin selectivity always exceeding 97%. Acetaldehyde production was consistently low, always below 0.1%, and not forming at all in one example. At any of the studied proportions, ethene selectivity remained between 0.05% and 0.2%.

Long-duration tests lasting 168 hours were conducted only with the 1:1 catalyst:co-catalyst mixture, with its performance compared to pure alumina (catalyst) over the same duration. These tests demonstrated the superiority of using the mixture, as deactivation of the pure catalyst was observed from approximately 35 hours onwards, while the catalyst and co-catalyst system remained stable throughout the 168 hours monitored. It is worth pointing out that when deactivation occurs, a gradual drop in alcohol conversion is noted. In the mentioned example, conversion fell from 99% at the start of the reaction to 90% at the end of 168 hours, when using only the catalyst. Using the mixture maintained conversion at 99% for the entire duration. This result indicates that the catalytic system described in this document can operate continuously without deactivation for a period more than five times longer than the useful life of the dehydration catalyst when used alone.

Catalyst deactivation is also clear for acetaldehyde production, which begins at about 1.5% selectivity, varying by values of up to 0.8% during the 168 hours using only the dehydration catalyst. When using the catalyst:co-catalyst mixture at a 1:1 ratio, the formation of acetaldehyde as a by-product was not observed throughout this entire period.

In addition to the products already mentioned, the formation of light products occurs, specifically CO, $CO_2$, $H_2$ and $CH_4$, in all cases, whether using only the catalyst or the catalytic system (catalyst and co-catalyst). However, there is a striking difference in acetone production as well when using the catalyst and co-catalyst mixture. This is the outcome of the oxy-ketonization reaction, transforming the acetaldehyde on the co-catalyst. Non-existent in known industrial ethanol dehydration processes using acid catalysts, acetone is formed with a selectivity of between 0.2% and 1%, depending on the type and proportion of co-catalyst used.

The advantage of removing the acetaldehyde and its transformation in situ—this conversion occurring in the dehydration reactor—by the acetone during the process consists of the chemical advantages of this molecule, as acetone is stable and less reactive under the reaction conditions. Furthermore, in terms of economic advantages, it is simple to separate the acetone from the final olefin stream, with its production also favoring production lines for other products, as it may be repurposed for other industrial uses (as an important solvent in the polymers and drugs segments) or for generating chemicals such as isopropanol and propene. Similarly, the concomitant reduction in ethane formation also endows the process with economic advantages through lowering associated separation costs.

For the purposes of analysis, a mass catalyst value interval of 11.4 to 11.8 mg was used, with a water:ethanol mass ratio of 3 for feeding into the process, operating condition at 470° C. for the reaction and a mass ratio of catalyst:inert matter (silicon carbide) of 0.0765. Short and long duration tests were conducted, lasting 14 hours and 168 hours respectively, the purposes of comparing catalyst deactivation and ethanol conversion.

Example 1

A gamma alumina type catalyst was combined with an yttrium oxide ($Y_2O_3$) in an alumina and oxide proportion of 1:1 and added into a stainless steel isothermal fixed bed Plug Flow Reactor (PFR) with an internal diameter of 0.9 cm. At atmospheric pressure and a temperature of 470° C., a feeder inflow of water and ethanol with a mass ratio of 3:1 to 44 mL/min was admitted into the reactor and left to react for a total period of 14 hours. When analyzing the effluent, it was noted that the ethanol conversion in this example was 99% and the selectivity levels for ethene, acetaldehyde and ethane varied between 97.6 to 98.9%, 0.09 to 0.17% and 0.15 to 0.20%, respectively.

Example 2

A gamma alumina type catalyst was combined with a zirconium oxide ($ZrO_2$) in an alumina and oxide proportion of 1:3 and added into a stainless steel isothermal fixed bed Plug Flow Reactor (PFR) with an internal diameter of 0.9 cm. At atmospheric pressure and a temperature of 470° C., a feeder inflow of water and ethanol with a mass ratio of 3:1 to 44 mL/min was admitted into the reactor and left to react for a total period of 14 hours. When analyzing the effluent, it was noted that the ethanol conversion in this example was 99.5% and the selectivity levels for ethene, acetaldehyde and ethane varied between 97.2% to 98.8%, 0.03% to 0.07% and 0.09% to 0.19%, respectively.

Example 3

A gamma alumina type catalyst was combined with a mixed lanthanum and zirconium oxide (La—$ZrO_2$) in an alumina and oxide proportion of 1:1 and added into a stainless steel isothermal fixed bed Plug Flow Reactor (PFR) with an internal diameter of 0.9 cm. At atmospheric pressure and a temperature of 470° C., a feeder inflow of water and ethanol with a mass ratio of 3:1 to 44 mL/min was admitted into the reactor and left to react for a total period of 14 hours. When analyzing the effluent, it was noted that the ethanol conversion in this example was 100% and the selectivity levels for ethene and ethane varied between 98% to 98.9% and 0.17% to 0.22%, respectively. The formation of acetaldehyde was not observed.

Example 4

A gamma alumina type catalyst was combined with a zirconium oxide with a monocline-type crystal structure (m-$ZrO_2$) in an alumina and oxide proportion of 1:1 and added into a stainless steel isothermal fixed bed Plug Flow Reactor (PFR) with an internal diameter of 0.9 cm. At atmospheric pressure and a temperature of 470° C., a feeder inflow of water and ethanol with a mass ratio of 3:1 to 44 mL/min was admitted into the reactor and left to react for a total period of 168 hours. When analyzing the effluent, it was noted that the ethanol conversion in this example was 99.8% throughout the entire reaction time (168 h) and the selectivity levels for ethene and ethane varied between 98.3% to 99.6% and 0.08% to 0.22%, respectively. There was no acetaldehyde formation throughout the entire reaction time.

The above-mentioned examples were summarized and compared as set forth in Table 1 below.

TABLE 1

| Example | 1 | 2 | 3 | 4 |
|---|---|---|---|---|
| Catalyst | γ-alumina | γ-alumina | γ-alumina | γ-alumina |
| Co-catalyst | $Y_2O_3$ | $ZrO_2$ | La-$ZrO_2$ | $ZrO_2$ |
| Proportion cat:co-cat (mass) | 1:1 | 1:3 | 1:1 | 1:1 |
| Reaction time (h) | 14 | 14 | 14 | 168 |
| Ethanol conversion (%) | 99 | 99.5 | 100 | 99.8 |
| Selectivity for ethene (%) | 97.6 to 98.9 | 97.2 to 98.8 | 98 to 98.9 | 98.3 to 99.6 |

TABLE 1-continued

| Example | 1 | 2 | 3 | 4 |
|---|---|---|---|---|
| Selectivity for acetaldehyde (%) | 0.09 to 0.17 | 0.03 to 0.07 | 0 | 0 |
| Selectivity for Ethane (%) | 0.15 to 0.20 | 0.09 to 0.19 | 0.17 to 0.22 | 0.08 to 0.22 |
| Selectivity for acetone (%) | 0.18 to 0.55 | 0.32 to 0.88 | 0.35 to 0.75 | 0.13 to 0.70 |

What is claimed is:

1. A catalytic system for the preparation of light olefins from ethanol, which comprises at least one ethanol-dehydration catalyst and at least one acetaldehyde-to-acetone catalyst,
wherein the ethanol-dehydration catalyst:acetaldehyde-to-acetone catalyst mass ratio is within a range of 1:0.5 to 1:5,
wherein the catalytic system exhibits an ethene selectivity of at least 97.2%,
wherein the ethanol-dehydration catalyst comprises gamma alumina,
wherein the acetaldehyde-to-acetone catalyst comprises at least one of $Y_2O_3$, $ZrO_2$, and $La-ZrO_2$, and
wherein the catalytic system, when present during a continuous operation of a preparation of light olefins, exhibits a reaction conversion of 99%, without deactivation, for a period more than five times longer than a useful life of the ethanol dehydration catalyst when used alone.

2. The catalytic system as recited in claim 1, wherein the catalytic system is a physical mixture of the ethanol-dehydration catalyst and acetaldehyde-to-acetone catalyst.

3. The catalytic system as recited in claim 1, wherein the catalytic system is a physical mixture of the ethanol-dehydration catalyst with the acetaldehyde-to-acetone catalyst presented as pellets of each one of the components in isolation, or a pellet made from a mixture of the two components laid out in sequential layers or beds, mixed or not, or in the form of powder, wherein the particles contain both the ethanol-dehydration catalyst and the acetaldehyde-to-acetone catalyst or individual particles of each one of the components.

4. The catalytic system as recited in claim 1, wherein the ethanol-dehydration catalyst:acetaldehyde-to-acetone catalyst mass ratio is within a range of 1:0.5 to 1:3.

5. A process for the production of light olefins from ethanol, the process comprising contacting the catalytic system as recited in claim 1 with a flow of alcohol, hydrated or not, in a reactor, at a temperature between 200° C. and 800° C. and a pressure between 1 bar and 60 bar.

6. The process as recited in claim 5, wherein temperature variations occur between 360° C. and 470° C.

7. The process as recited in claim 5, wherein pressure variations occur between 1 bar and 20 bar.

8. The process as recited in claim 5, wherein the alcohol is a hydrated alcohol having a water:alcohol mass ratio of between 0.25:1 and 5:1.

9. The process as recited in claim 5, wherein the reaction occurs in a Plug Flow Reactor (PFR), fixed or fluid bed, batch or a Continuous-Stirred Tank Reactor (CSTR), being adiabatic or not.

10. The process as recited in claim 5, wherein the catalytic system operates continuously, maintaining the reaction conversion at 99%, without deactivation, for a period more than five times longer than the useful life of the dehydration catalyst when used alone.

11. The process as recited in claim 5, wherein the hydrated alcohol has a water:alcohol mass ratio of between 1:1 and 3:1.

* * * * *